United States Patent [19]

Berghagen

[11] Patent Number: 4,606,063
[45] Date of Patent: Aug. 12, 1986

[54] SHUTTER ARRANGEMENT FOR USE IN INTRA-ORAL RADIOGRAPHY

[76] Inventor: Nils Berghagen, Godsü garvägen 47, S-121 63 Johanneshov, Sweden

[21] Appl. No.: 662,402
[22] PCT Filed: Feb. 3, 1983
[86] PCT No.: PCT/SE83/00038
 § 371 Date: Sep. 25, 1984
 § 102(e) Date: Sep. 25, 1984
[87] PCT Pub. No.: WO84/03033
 PCT Pub. Date: Aug. 16, 1984

[51] Int. Cl.⁴ .............................................. G03C 9/00
[52] U.S. Cl. ..................................... 378/41; 378/148; 378/150; 378/170
[58] Field of Search ................ 378/170, 148, 150, 41, 378/42

[56] References Cited

U.S. PATENT DOCUMENTS

| | | | |
|---|---|---|---|
| 3,745,344 | 7/1973 | Updegrave | 378/170 |
| 4,109,156 | 8/1978 | Schroeder | 378/148 |
| 4,166,220 | 8/1979 | Stutts | 378/148 |
| 4,221,971 | 9/1980 | Burger | 378/148 |
| 4,507,798 | 3/1985 | Welander | 378/170 |

Primary Examiner—Craig E. Church
Assistant Examiner—T. N. Grigsby
Attorney, Agent, or Firm—Kinzer, Plyer, Dorn & McEachran

[57] ABSTRACT

A shutter arrangement for intra-oral radiographic X-ray apparatus comprises a substantially punctiform X-ray source (1), a radiation-screening and radiation-directing X-ray tube (3), a holder (10) for holding an object and an X-ray film or plate, the holder being located externally of the X-ray radiation exit orifice of the X-ray tube, and being adjustable in at least two positions in a direction transversely of the direction of radiation, for producing at least two pictures of the object in two mutually different positions relative to the radiation direction. The arrangement also includes a shutter (7c) which is arranged between the X-ray source (1) and the holder (10) and which has a shutter aperture which is adapted to the size of the X-ray film or plate used. The shutter (7c) comprises an apertured metal plate arranged in the exit orifice of the X-ray tube (3) for displacement in a slide-track arrangement (6), in a direction transversely to the direction of the radiation. The slide-track arrangement (6) and the metal plate (7c) are provided with mutually co-acting means (8), which define snap-in locations of the metal plate corresponding to selected positions of the holder (10).

3 Claims, 5 Drawing Figures

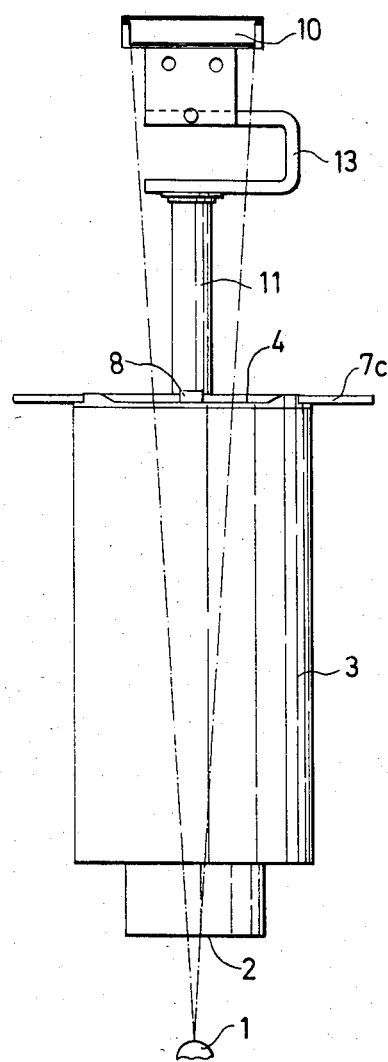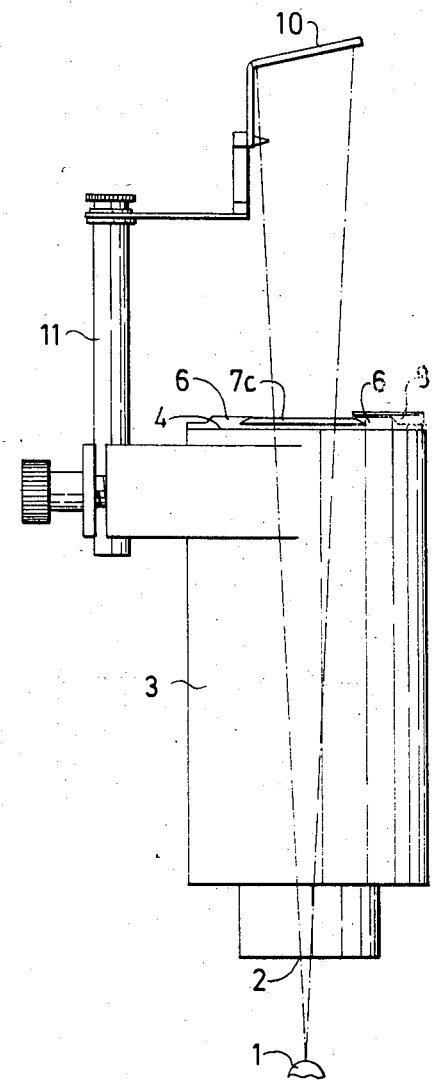

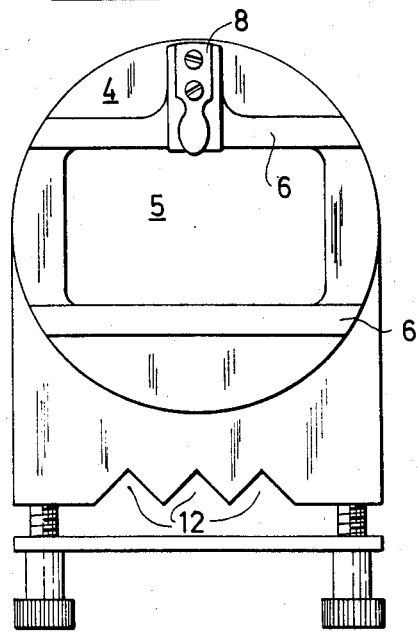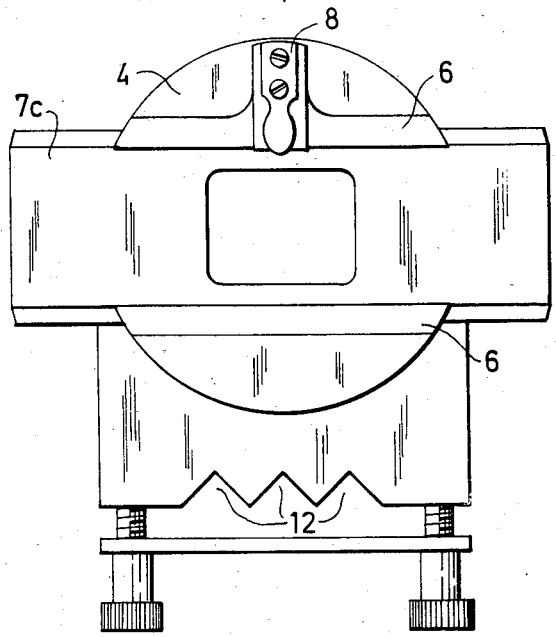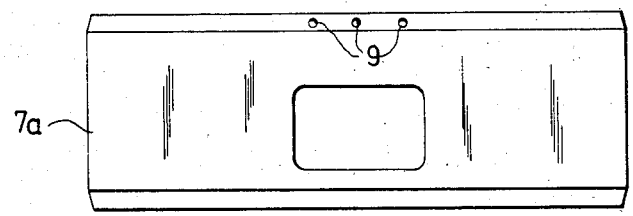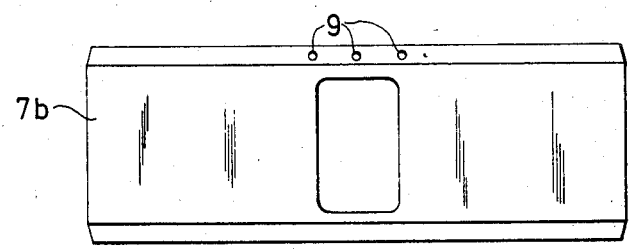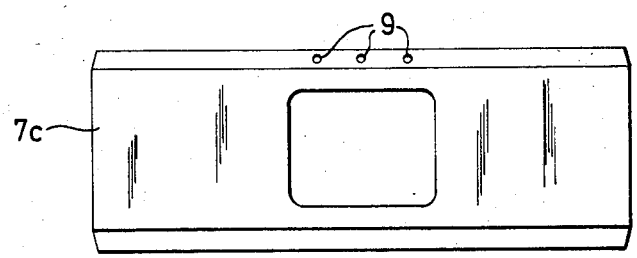

SHUTTER ARRANGEMENT FOR USE IN INTRA-ORAL RADIOGRAPHY

The present invention relates to a shutter arrangement for intra-oral radiographic X-ray apparatus of the kind which comprise a punctiform X-ray source; a radiation screening and directing X-ray tube; a holder for an object and for an X-ray film or plate, located externally of the radiation-exit orifice of the X-ray tube, said holder being adjustable to at least two positions in a direction transversely to the direction of the radiation, to produce at least two images of the object in two different positions relative to the radiation, for example for stereoscopic reproduction in dental diagnosis; and a shutter which is arranged between the X-ray source and the holder and which has a shutter aperture which is adapted to the size of the X-ray film or plate, whereby the shape and size of the beam passing through the aperture substantially coincides with the shape and size of the film or plate, in the plane thereof.

One disadvantage with such known shutter arrangements is that the clarity of the picture obtained is not always satisfactory, for example is blurred as a result of movement. Another disadvantage is that the amount of X-ray radiation to which the patient is subjected is relatively high. Consequently, an object of the present invention is to provide a shutter arrangement by means of which these and other disadvantages inherent with known shutter arrangements of the aforementioned kind can be overcome.

Accordingly, this invention consists in a shutter system of the kind described in the introduction, characterized in that the shutter comprises a metal plate which is provided with a shutter aperture and which is mounted in the exit orifice of the X-ray tube in a manner which enables it to be displaced in a slide path transversely to the beam direction, said slide path and said metal plate being provided with mutually co-acting means which define snap-in locations for the metal plate and which correspond to respective positions of the holder.

In a further embodiment of the invention, in which the holder can be adjusted between at least two fixed positions of alignment lying in a plane entending perpendicularly to a central beam of radiation in the beam bundle, the shutter is arranged so that when being adjusted from one position to another it moves in parallel in a plane parallel with said perpendicular plane.

When using the shutter arrangement according to the invention, the quality of the three-dimensional X-ray pictures obtained is considerably improved, inter alia because there is no blurring due to movement. The shutter arrangement according to the invention also permits smaller radiation dosages to be administered than was hitherto the case.

So that the invention will be more readily understood and further features thereof made apparent, an exemplary embodiment of the invention will now be described with reference to the accompanying drawings, in which FIG. 1 illustrates schematically and in plan view an X-ray apparatus provided with a shutter system according to the invention;

FIG. 2 is a side view of the apparatus illustrated in FIG. 1;

FIG. 3 illustrates the shutter system with the metal plate fitted;

FIG. 4 illustrates the shutter arrangement with the metal plate inserted; and

FIG. 5 illustrates three mutually different metal plates which are included in the shutter arrangement.

The ancillary apparatus for intra-oral radiography comprises three major parts, namely a holder 10 provided with a bite plate, a film-holder shaft 11, and a shutter arrangement incorporated in the X-ray beam exit orifice 5 of the X-ray tube 3. The X-ray beams are derived from a beam source 1, and are allowed to pass through a close-up shutter 2 in the inlet orifice of the X-ray tube.

The film holder 10 is made of metal and comprises the aforementioned bite plate and a back piece, into which the film or plate is inserted. As will be seen from FIG. 2, The back piece forms an obtuse angle with the bite plate, so that the film can be comfortably placed in the jaw region of the patient. Means (not shown) are provided for locking the bite plate firmly to the holder shaft 11 in a selected position relative to said shaft. The holder shaft 11 includes a part 13 which can be pivoted to the left or to the right and which can be locked in a selected position to the remainder of the shaft. The shaft 11 is mounted on an attachment located on the outer edge of the X-ray tube 3. As illustrated in FIGS. 3 and 4, the shutter arrangement is provided with three fixing locations 12, each of which is arranged to co-act with a corresponding fixing means on a respective shutter plate, as described more clearly hereinafter, and which permit a mesial, a distal excentric and an ortho-radial picture respectively to be taken. In this respect, the X-ray source can be moved parallel to the plane of the film, which means that only horizontal parallax exists. The images can therefore be used for stereo-viewing.

Arranged in the exit orifice of the X-ray tube 3 is a metal plate 4 having arranged centrally therein an aperture 5, through which beams of X-rays from the source 1 can pass. The plate 4 is provided with a slide-track arrangement 6, for receiving a rectangular plate 7a, 7b or 7c. Each of the rectangular plates 7a, 7b or 7c is provided with a window which is different from the windows of the other rectangular plates and which corresponds to a particular size of film. In this way, only the actual image surface need be irradiated. Thus, when the plate containing the appropriate window for the film being used is inserted in position in the slide-track arrangement 6, the central aperture 5 is made smaller, as a result of the window in said plate.

In the FIG. 5 embodiment, three plates 7a, 7b and 7c, are provided. The size of respective windows is coordinated with the size of the film in plane, so that when taking an X-ray picture, only the film plane is irradiated. The plate 7a, 7b or 7c, which are suitably made of metal, such as brass, are automatically locked in position in the slide-track arrangement 6 by means of a snap-in fastener means 8, which can be snapped into a selected one of three different snap-in locations 9 on the metal plates, to bring a respective plate into a selected one of the aforementioned three fixing positions 12. In this respect, the snap-in locations are coordinated with the position of the film and the object in relation to the position of the X-ray source 1, when taking stereographic pictures. Suitably, each of the snap-in locations 9 is labled with a colour notation or some other identifying means, corresponding to a similar colour notation given to the fixing positions 12, to facilitate the use of the shutter arrangement.

The automatic functioning of the shutter arrangement is made possible by the fact that during the exposure period, the radiation source 1, the X-ray tube 3 and the film holder 10, to which the patient's teeth and jaw are fixed through the shaft 11, form a fixed camera system.

The advantages afforded include a flat film surface, no blurring of the image due to movement, which results in the high-quality picture, and a reduction in the dosage of X-ray radiation and secondary radiation subjected to the patient.

Although not specifically shown, the film holder (10) is preferably provided with means which enable it to be readily changed and to be locked firmly to the X-ray tube during the exposure period.

As will be understood from the aforegoing, the apparatus has the form of a fixed and rigid "camera system", especially suited for X-ray radiography, said apparatus affording the following advantages:

(a) the film is held flat while taking an X-ray picture;

(b) because all movement is prevented, the resultant picture is clear and distinct; and (c) only the film plane is irradiated when taking an X-ray picture, thereby reducing the amount of radiation to which the patient is subjected.

I claim:

1. A method of creating stereophotographic X-ray pictures of a tooth for dental diagnosis purposes including the steps of:

positioning a tooth on a bite plate with the tooth lying on a first axis extending from the tooth through a shutter aperture of a shutter and an X-ray radiation screening and directing tube to a puntiform X-ray source, taking an X-ray picture of the tooth along said first axis, transversely moving the bite plate relative to the tube, moving the shutter aperture transversely in the same direction as the bite plate, but a shorter distance to align the shutter aperture along a second axis between the bite plate and the puntiform X-ray source, which second axis extends at an angle relative to the first axis, and taking another X-ray picture of the tooth to provide a pair of X-ray pictures which can be used to provide a stereographic view of the tooth.

2. An apparatus for creating stereographic X-ray pictures of a tooth, including:

an X-ray radiation screening and directing tube, a substantially puntiform X-ray source at one end of the tube, a bite plate located at the other end of the tube, a shutter having a shutter orifice located between the tube and the bite plate, and means to independently move the bite plate and the shutter orifice transversely of the tube to align the shutter orifice with the X-ray source and the bite plate in the transversely moved position of the bite plate.

3. The apparatus of claim 3 in which the means to independently move the bite plate and shutter orifice transversely of the tube includes a support shaft for the bite plate, a bracket extending transversely from the tube, a plurality of support shaft engaging notches formed along the bracket in the direction transverse of the tube, means to lock the support shaft in a selected one of the notches formed on the bracket, means to selectively lock the shutter aperture in one of a plurality of positions extending transversely of the tube which positions align with the notches formed on the bracket.

* * * * *